United States Patent
Nicola et al.

[11] Patent Number: 6,004,636
[45] Date of Patent: Dec. 21, 1999

[54] MEDICAL BAG

[75] Inventors: Thomas Nicola, Spicheren, France; Thomas Kreischer, Saarbrücken, Germany

[73] Assignee: Fresenius AG, Bad Homburg, Germany

[21] Appl. No.: 08/722,531

[22] Filed: Sep. 27, 1996

[30] Foreign Application Priority Data

Sep. 29, 1995 [DE] Germany .......................... 195 36 546

[51] Int. Cl.$^6$ .................................. A61J 1/10; A61J 1/14
[52] U.S. Cl. ........................ 428/35.2; 428/35.5; 428/192; 604/29; 604/262; 604/408; 604/409; 128/DIG. 24; 383/22
[58] Field of Search .................................. 428/35.2, 35.5, 428/521, 523, 192; 604/403, 408, 409; 383/116, 22, 24; 128/912, DIG. 24

[56] References Cited

U.S. PATENT DOCUMENTS

| 3,211,144 | 10/1965 | Nehring | 604/409 |
| 4,803,102 | 2/1989 | Raniere et al. | 422/35.2 |

FOREIGN PATENT DOCUMENTS

| 2163022 | 10/1995 | Canada . |
| 0114964 | 11/1983 | European Pat. Off. . |
| 0114964A1 | 8/1984 | European Pat. Off. . |
| 0345774A1 | 12/1989 | European Pat. Off. . |
| 0380145A1 | 8/1990 | European Pat. Off. . |
| 0437856A2 | 7/1991 | European Pat. Off. . |
| 0513364A1 | 11/1992 | European Pat. Off. . |
| 0619998A1 | 10/1994 | European Pat. Off. . |
| 0635254A1 | 1/1995 | European Pat. Off. . |
| 2523847 | 9/1983 | France . |
| 2544612 | 10/1984 | France . |
| 3919360A1 | 12/1990 | Germany . |
| 4410876A1 | 10/1995 | Germany . |
| PCT/US88/00739 | 3/1988 | WIPO . |
| PCT/US93/02016 | 3/1993 | WIPO . |

*Primary Examiner*—Rena L. Dye
*Attorney, Agent, or Firm*—Fulbright & Jaworski L.L.P.

[57] ABSTRACT

An empty medical bag which is heat sterilized and made of a matrix-phase polymer system. After heat sterilization at 121° C., the inside surfaces do not adhere to each other.

20 Claims, 1 Drawing Sheet

MEDICAL BAG

TECHNICAL FIELD OF THE INVENTION

The invention concerns a medical bag with one chamber and one tubular connecting piece.

BACKGROUND OF THE INVENTION

Bags made of thermoplastic materials are usually not heat-sterilizable when empty since the inside surfaces of the bag, which have optimum sealing properties, are frequently in intimate contact with each other due to heat sterilization and even adhere to each other. With customary hot steam sterilization at a temperature of approximately 121° C., such a clinging together of the inside surfaces of such bags is thus the rule such that only little liquid may be introduced into these bags, unless the liquid is added to the bag chamber under elevated pressure. However, even with such pressure treatment it is not possible to guarantee that tightly adhering points will be released.

To combat adhesion at relatively large areas of the surfaces, bag films have been mechanically pretreated in the prior art. Thus, for example, the surfaces have been roughened or raised points have been incorporated into the surfaces, for example, punctiform bumps, grooves, or ridges. The result is that the inside surfaces only cling to each other in a small surface area such that these areas are then released upon filling.

U.S. Pat. No. 3,211,144, for example, prevents the cohesion of the inside surfaces in that at least one of the inside surfaces is roughened by the use of a roller with an appropriately designed surface.

Etching or sandblasting are mentioned as other possibilities for roughening the surface such that there is no longer adhesion of the inside surfaces.

However, such treatment of the film surfaces is very time consuming and costly.

Consequently, medical bags are still primarily heat sterilized using the method whereby the bag is filled before sterilization with air or liquid such as water or already filled with the medical fluid to be used, and heat sterilization is then undertaken. Such a process is also disclosed in EP-A1-0 114 964. There, medical containers formed by sealing films made of a polymer mixture are described. Before sterilization, the containers are filled with air, water, or a medical fluid.

SUMMARY OF THE INVENTION

The object of the invention is to make available a medical bag which, after heat sterilization when empty, does not have inside surfaces intimately contacting each other or even surfaces adhering together, without the bag films having been mechanically pretreated or provided with raised points. It is further the object of the invention to make available medical bags which may be used directly as empty bags after heat sterilization when empty.

The object is accomplished through the subject of claim 1. Advantageous embodiments of the invention are described in claims 2 through 6.

DETAILED DESCRIPTION OF THE INVENTION

Figure 1:
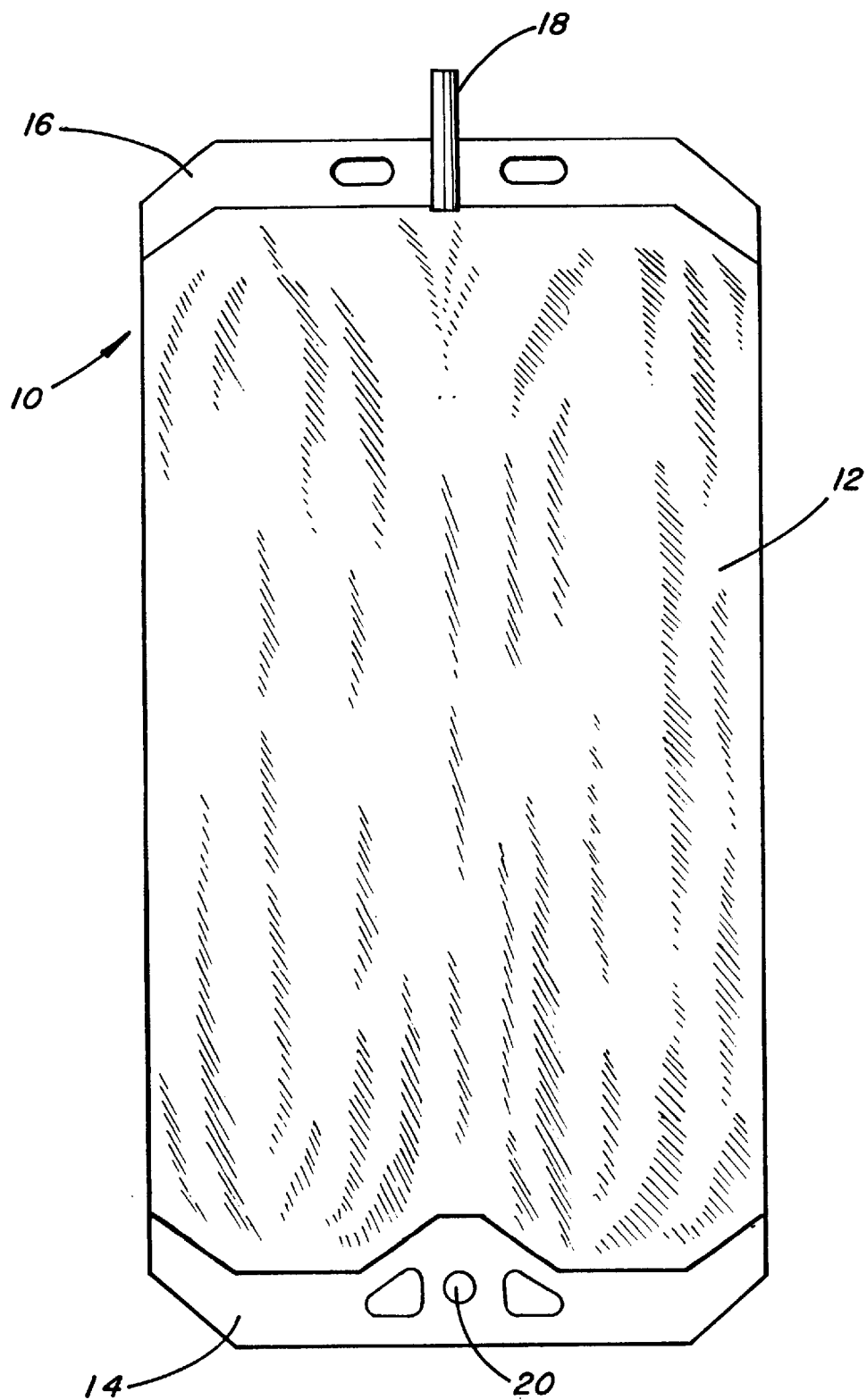
FIG. 1 presents a schematically simplified depiction of a bag according to the invention.

The object of the invention is to make available a medical bag which, after heat sterilization when empty, does not have inside surfaces intimately contacting each other or even surfaces adhering together, without the bag films having been mechanically pretreated or provided with raised points. It is further the object of the invention to make available medical bags which may be used directly as empty bags after heat sterilization when empty.

The object is accomplished through the subject of claim 1. Advantageous embodiments of the invention are described in claims 2 through 6.

Surprisingly, it has now been discovered that the matrix-phase polymer system described in DE 44 10 876 results in a medical bag, which, without further processing of the film, is heat sterilizable when empty, whereby the inside surfaces do not adhere to each other after sterilization.

Consequently, such a medical bag may be used advantageously for drainage purposes in urology or in peritoneal dialysis. Such bags must always be sterilized since they are connected to the patient's body via tubes or catheters, such that possible contaminations of the bag may be hazardous to health.

Preferably, so-called blown or even tubular films are used to fabricate the bag. These may possibly be folded and merely have to be closed, i.e., sealed, on two sides of the outer border, i.e., at the two openings. However, the use of individual sheets of film, which, however, have to be sealed all the way around, is also conceivable.

The film has, at least in the inner layer, which is also the sealing layer, essentially two components, i.e., a matrix polymer and a phase polymer. The system of matrix and phase polymers is referred to hereinafter as the matrix-phase polymer system.

Polymers with a high excitation or melting temperature range, such as polyethylene homopolymer, polypropylene homopolymer, and polypropylene copolymer may be used as matrix polymers. Polyethylene is used as high density polyethylene (HDPE). Of the matrix polymers mentioned, the polypropylene copolymer is preferred. Particularly preferred is a polypropylene random copolymer.

Only polymers with a likewise high excitation range, such as styrene ethylene/butylene styrene block polymer (SEBS), styrene ethylene/propylene styrene block polymer (SEPS), and/or styrene isoprene styrene triblock polymer (SIS) may be used as phase polymers. Preferably, styrene ethylene butylene styrene block copolymer is used. The proportion of the phase polymer in the polymer layer should be in the range from 1 to 40 wt.-%, based on the total matrix-phase polymer system.

A matrix polymer system which contains propylene as a matrix polymer is preferred. This matrix polymer is advantageously present in a quantity of 60–90 wt.-%. Further preferred as a phase polymer is styrene ethylene butylene styrene block copolymer (SEBS) or styrene ethylene propylene styrene block copolymer (SEPS), which are present in a quantity of 2–40 wt.-%. Preferably, these phase polymers have a molecular weight above 100,000 g/mol and have no significant diblock components.

The seam of the outer border zone has at least one support as a connecting piece in at least one chamber, whereby this support is an intake support.

The bag may include a suspension arrangement and/or a point/tapering area.

The process for fabrication of the empty chamber medical bag according to the invention is characterized in that the sealing is performed on the outer border zone at such a temperature that no tearing of the sealed zone or destruction of the bag is any longer permitted.

The duration of the sealing procedure is preferably in the range from 1 to 8 seconds, and the surface pressure exerted on the zones to be sealed during the sealing procedure is preferably in the range from 0.1 to 3 N/mm². However, for both parameters mentioned, values outside the ranges mentioned are also possible. Both parameters are thus not restricted to the preferred ranges.

Additional details, characteristics, and advantages of the invention are presented in the following description of an exemplary embodiment with reference to the drawing.

It depicts:

FIG. 1 presents a schematically simplified depiction of a bag according to the invention.

FIG. 1 depicts a bag 10 with a chamber 12.

This bag 10 is formed from a blown film such that only the upper border zone 14 and the lower border zone 16 are sealed through. A connecting support 18, which is tubular and forms a flow connection with the chamber 12, is sealed into the border zone 16. This connecting piece 18 may be linked with a tube (not shown) or another connecting piece.

The upper border has a suspension arrangement 20 such that the bag 10 may be hung if necessary.

The bag film is produced on a coextrusion blown film system.

The following blown film is manufactured:

85 wt.-% PP-homopolymer with a softening point above 121° C. (Novolen 3200 HX from BASF) is compounded with 15 wt.-% SEBS (Kraton G 1650 from Shell) and then processed on the blown film system into a blown film.

Then, the blown film is cut according to the length of the bag and further made into a bag, as shown in FIG. 1. In the process, the sealing zones 14 and 16 are sealed at approx. 140° C.

If such a bag is filled with 3 to 4 l of water at room temperature and dropped from a height of 2 m, this bag does not burst. It also meets the requirement of transparency for monitoring the substance filling it.

As long as these properties are met, the actual film structure is variable; and the required property of heat sterilization without clinging or adhering tendencies depends only on the use of the phase-matrix polymer system.

The rigidity and strength of the film depends on its thickness. This is usually in the range from 0.1 to 0.3 mm and may, as necessary, also fall outside these limits.

A bag 10 produced in this manner is also surprisingly well suited to incorporation into a CAPD [continuous ambulatory peritoneal dialysis] tube system as an empty bag. It is connected via a tube to a peritonea dialysis catheter of a patient and must for these reasons be absolutely sterile. Consequently, the entire system is placed in a containment bag and then heat sterilized in a heat sterilization system at 121° C. in the customary manner.

We claim:

1. A medical bag (10), having smooth confronting surfaces which has been obtained without mechanical pretreatment of the inside surfaces or provision of raised points and which has been heat sterilized in an empty state with at least portions of its inner surfaces in contact, said medical bag possessing at least one chamber (12) and at least one tubular connection (18), and suspension means (20), the inner film surface of said medical bag consists of substantially a blend of a matrix polymer and of a phase polymer, a matrix-phase polymer system and the border zone (14, 16) of said medical bag being sealed, characterized in that the inside surfaces of the medical bag do not adhere to each other after heat sterilization when empty.

2. The bag according to claim 1 characterized in that the matrix polymer of the matrix-phase polymer system is a polyethylene homopolymer, a propylene homopolymer, or a propylene copolymer.

3. The bag according to claim 2, characterized in that the matrix polymer is a propylene copolymer.

4. The bag according to claim 1, characterized in that the phase polymer of the matrix-phase polymer system is a styrene ethylene/butylene styrene triblock polymer (SEBS), a styrene ethylene/butylene styrene triblock polymer (SEBS) with a styrene ethylene/butylene styrene diblock component (SEB), a styrene ethylene/propylene styrene triblock polymer (SEPS), a styrene butadiene styrene triblock polymer (SBS) or a styrene isoprene styrene triblock polymer (SIS) or an ethylene-α-olefin copolymer or a blend of two or three of said polymers.

5. The bag according to claim 1 characterized in that the proportion of the phase polymer in the polymer system is in the range from 1 through 40 wt %, based on the matrix-phase polymer system.

6. The bag according to claim 2 characterized in that the proportion of the phase polymer in the polymer system is in the range from 1 through 40 wt %, based on the matrix-phase polymer system.

7. The bag according to claim 3 characterized in that the proportion of the phase polymer in the polymer system is in the range from 1 through 40 wt. %, based on the matrix-phase polymer system.

8. The bag according to claim 4 characterized in that the proportion of the phase polymer in the polymer system is in the range from 1 through 40 wt. %, based on the matrix-phase polymer system.

9. The bag according to claim 1 characterized in that the film is multilayered and coextruded.

10. The bag according to claim 2 characterized in that the film is multilayered and coextruded.

11. The bag according to claim 3 characterized in that the film is multilayered and coextruded.

12. The bag according to claim 4 characterized in that the film is multilayered and coextruded.

13. The bag according to one of claims 1 through 4, characterized in that the proportion of the phase polymer in the polymer system is in the range from 1 through 40 wt. %, based on the matrix-phase polymer system.

14. The bag according to one of claims 1 through 4, characterized in that the film is multilayered and coextruded.

15. The bag according to claim 3, characterized in that the matrix polymer is a propylene random copolymer.

16. The bag according to claim 13, characterized in that the proportion of the phase polymer in the polymer system is in the range from 10 through 20 wt. %, based on the matrix-phase polymer system.

17. The bag according to claim 5, characterized in that the proportion of the phase polymer in the polymer system is in the range from 10 through 20 wt. %, based on the matrix-phase polymer system.

18. The bag according to claim 6, characterized in that the proportion of the phase polymer in the polymer system is in the range from 10 through 20 wt. %, based on the matrix-phase polymer system.

19. The bag according to claim 7, characterized in that the proportion of the phase polymer in the polymer system is in the range from 10 through 20 wt. %, based on the matrix-phase polymer system.

20. The bag according to claim 8, characterized in that the proportion of the phase polymer in the polymer system is in the range from 10 through 20 wt. %, based on the matrix-phase polymer system.

* * * * *